United States Patent

Sarantakis

[11] 4,309,340
[45] Jan. 5, 1982

[54] POLYPEPTIDE COMPOSITIONS

[75] Inventor: Dimitrios Sarantakis, West Chester, Pa.

[73] Assignee: American Home Products Corporation, New York, N.Y.

[21] Appl. No.: 135,420

[22] Filed: Mar. 31, 1980

[51] Int. Cl.$^3$ .......................................... C07C 103/52
[52] U.S. Cl. .............................................. 260/112.5 R
[58] Field of Search ................................. 260/112.5 R

[56] References Cited

U.S. PATENT DOCUMENTS 4,190,646  2/1980  Goldstein et al. ........... 260/112.5 R

OTHER PUBLICATIONS

Goldstein et al., Science, 204, (1979), 1309–1310.

Primary Examiner—Delbert R. Phillips
Attorney, Agent, or Firm—George Tarnowski

[57] ABSTRACT

There are disclosed polypeptides having the following formula:

R-X$_1$-Lys-X$_3$-Val-X$_5$-R$_1$ wherein
  R is hydrogen, alkanoyl of 1–4 carbon atoms or aroyl of 6–10 carbon atoms;
  X$_1$ is L-Arg, D-Arg or D-homoarginine;
  X$_3$ is Asn, Gln or the N-substituted carboxamides thereof;
  X$_5$ is L- or D-Tyr, L- or D-Phe, L- or D-Trp, L- or D-Leu, L- or D-Met, D-Met-ol-oxide or D-Phe-ol;
and
  R$_1$ is amino, monoalkylamino of 1–4 carbon atoms, dialkylamino of 1–4 carbon atoms, hydroxy, alkoxy of 1–4 carbon atoms,

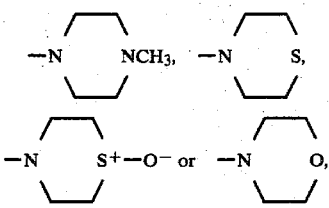

the fully protected peptide-resin intermediates thereof, or pharmaceutically acceptable salts thereof. These polypeptides have the capability of inducing the differentiation of T-lymphocytes and thus are useful in a number of therapeutic areas.

4 Claims, No Drawings

POLYPEPTIDE COMPOSITIONS

BACKGROUND OF THE INVENTION

Recent research has established the involvement of the thymus in the functioning of the immune system in mammalian species. It is in the thymus that haemopoietic stem cells become differentiated to mature immunocompetent lymphocytes called T-cells, which circulate to the blood, lymph, spleen and lymph nodes. The T-cells have immunological specificity and are involved in the cell-mediated immune responses, such as graft responses, response to viral infections, response to neoplasms and so forth. The body's response to antigenic material, such as for example in response to bacterial attack, is the province of antibody secreting cells, called B-cells, which are derived from bone marrow stem cells, but which are not differentiated in the thymus. The antibody response to an antigen, in many cases, requires the presence of appropriate T-cells, so that T-cells, and consequently the thymus, are necessary for the body's immune system to make not only cellular immunity responses, but also humoral antibody response. The thymic induction of the necessary differentiation of stem cells to T-cells is mediated by secretions of thymic hormones by the epithelial cells of the thymus.

The great interest in thymic substances, which may be implicated in various aspects of the immune response, has been instrumental in creating a very productive research effort. As a result of this research, a number of thymic substances have been reported in the literature. In the article by Goldstein and Manganaro in *Annals of the New York Academy of Sciences*, Volume 183, pps. 230–240, 1971, there are disclosures regarding the presence of a thymic polypeptide which causes a myasthenic neuromuscular block in animals, which is analogous to the human disease of myasthenia gravis. Further, in this article it was discovered that two distinct effects were caused by separate polypeptides in bovine thymus. One of these polypeptides, named "thymotoxin", was believed to cause myositis but it was further indicated that this polypeptide had not been isolated although it appeared to be a polypeptide of approximately 7,000 molecular weight, had a strong net positive charge and was retained on CM-Sephadex at a pH of 8.0.

In the publication "Nature", 247, 11, Jan. 4, 1975, there are described products identified as Thymin I and Thymin II which were found to be new polypeptides isolated from bovine thymus which have particular uses in various therapeutic areas. Because of the use of similar names for other products isolated from the thymus in the prior art, these Thymin I and Thymin II products are now named as Thymopoietin I and Thymopoietin II. These products and processes are described in U.S. Pat. No. 4,077,949. In U.S. Pat. No. 4,002,602 there are disclosed long chain polypeptides described as Ubiquitous Immunopoietic Polypeptides (UBIP), which polypeptide is a 74-amino acid polypeptide characterized by its ability to induce in vitro, in nanogram concentrations, the differentiation of both T-cell and B-cell immunocytes from precursors present in bone marrow or spleen. Thus, the polypeptide is useful in therapeutic areas involving thymic or immunity deficiencies and the like.

In U.S. Pat. No. 4,002,740 there are disclosed synthesized tridecapeptide compositions which have the capability of inducing the differentiation of T-lymphocytes but not of complement receptor B-lymphocytes. This polypeptide thus exhibited many of the characteristics of the long chain polypeptides isolated and named as thymopoietin in above-mentioned U.S. Pat. No. 4,077,949.

In U.S. Pat. No. 4,190,646, there are disclosed pentapeptides having the basic amino acid sequence:

R-NH-Arg-Lys-Asp-Val-Tyr-COR[1]

wherein R and R[1] are substituents which do not substantially affect the biological activity of the basic active sequence. In the publication "Science", 204, 1309 (1979), it is disclosed that this pentapeptide arginyl-lysyl-aspartyl-valyl-tyrosine corresponds to amino acid residues 32–36 in thymopoietin and that in vitro this pentapeptide induced the differentiation of murine prothymocytes to thymocytes and inhibited differentiative induction of cells of the B lineage, which is a combination of actions that is unique to the parent molecule thymopoietin. In vivo it displayed the further thymopoietin property of reducing the high numbers of autologous rosette-forming cells normally present in the spleens of athymic mice.

The present invention relates to novel polypeptides having the ability to induce differentiation of T-lymphocytes.

DESCRIPTION OF THE INVENTION

In accordance with this invention, there is provided a novel group of pentapeptides having the structural formula:

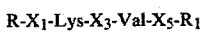
$$R-X_1-Lys-X_3-Val-X_5-R_1$$

wherein

R is hydrogen, alkanoyl of 1–4 carbon atoms or aroyl of 6–10 carbon atoms;

$X_1$ is L-Arg, D-Arg or D-homoarginine;

$X_3$ is Asn, Gln or the N-substituted carboxamides thereof;

$X_5$ is L- or D-Tyr, L- or D-Phe, L- or D-Trp, L- or D-Leu, L- or D-Met, D-Met-ol-oxide or D-Phe-ol;

and $R_1$ is amino, monoalkylamino of 1–4 carbon atoms, dialkylamino of 1–4 carbon atoms, hydroxy, alkoxy of 1–4 carbon atoms,

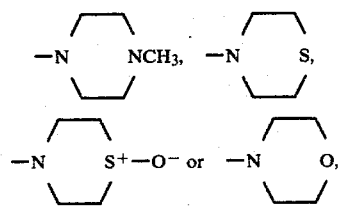

the fully protected peptide-resin intermediates thereof, or pharmaceutically acceptable salts thereof.

As a further embodiment, there are provided pentapeptides having the same structural formula as above and in which:

R is hydrogen, alkanoyl of 1–4 carbon atoms or aroyl of 6–10 carbon atoms;

$X_1$ is L-Arg, D-Arg or D-homoarginine;

X$_3$ is Asn, Gln or the N-substituted carboxamides thereof;

X$_5$ is L- or D-Phe, L- or D-Trp, L- or D-Leu, L- or D-Met, D-Met-ol-oxide or D-Phe-ol; and R$_1$ is amino, monoalkylamino of 1-4 carbon atoms, dialkylamino of 1-4 carbon atoms, hydroxy, alkoxy of 1-4 carbon atoms,

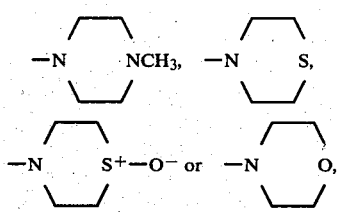

the fully protected peptide-resin intermediates thereof, or pharmaceutically acceptable salts thereof.

The N-substituted carboxamides of Asn and Gln in position X$_3$ are mono- and di-alkyl substituted, in which the alkyl groups have 1-4 carbon atoms.

In the depicted formula and throughout the specification and claims, where the chirality of an amino acid is not indicated or otherwise stated, it is understood to be of the L-series.

The fully protected peptide-resin intermediates, which comprise an additional aspect of the invention, may be depicted as follows:

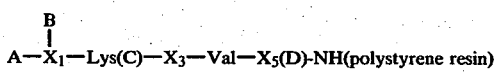

wherein X$_1$ and X$_3$ as as defined hereinbefore; X$_5$ is L- or D-Tyr, L- or D-Phe, L- or D-Trp, L- or D-Leu, L- or D-Met, D-Met-ol-oxide or D-Phe-ol; and A, B, C, and D are protecting groups which are hereinafter described. These intermediates comprise the fully protected pentapeptide bound to a benzhydrylamine polystyrene resin support employed in the solid phase synthesis of the polypeptide.

The pharmaceutically acceptable salts of the compounds of the invention are those non-toxic addition salts produced by known methods from acids conventionally employed with pharmaceuticals such as hydrochloric, hydrobromic, sulfuric, phosphoric, polyphosphoric, maleic, acetic, citric, benzoic, succinic, malonic, ascorbic or the like.

The peptides of the invention are able to directly induce the proliferation of T-cells in concentrations of about 1-200 ng/ml. The high activity of the compounds at such very low concentrations makes them useful in the therapeutical treatment of a number of disorders which involve the immune response. Of course, because the compounds perform certain of the thymic functions, they have application in various thymic function and immunity areas. A primary field of a application is in the treatment of DiGeorge Syndrome, a condition in which there is a congenital absence of thymus. Injection of the polypeptides will overcome this deficiency. The polypeptides will increase or assist in therapeutic stimulation of cellular immunity and thereby become useful in the treatment of diseases involving chronic infection in vivo, such as fungal or mycoplasma infections, tuberculosis, leprosy, acute and chronic viral infections, and the like. Further, the compounds are considered to be useful in any area in which cellular immunity is an issue and particularly where there are deficiencies in immunity such as in the DiGeorge Syndrome mentioned above. Also, where there is an excess of antibody production due to unbalanced T-cells and B-cells, the compounds can correct this condition by stimulating T-cell production. Thus, they may be of therapeutic use in certain autoimmune diseases in which damaging antibodies are present, for example, systemic lupus erythematosus. The polypeptides are also useful in inhibiting the uncontrolled proliferation of Thymopoietin-responsive lymphocytes.

An important characteristic of the polypeptides is their in vivo ability to restore cells with the characteristic of the T-cells. Therefore, the polypeptides of this invention are active in many areas as a result of their ability to enhance the immune response in the body. Also, the peptides of this invention are highly active in very low concentrations ranging from 1 nanogram per ml., and are maximally active at concentrations from about 200 nanograms per ml. The carrier may be any of the well known carriers for this purpose including normal saline solutions, preferably with a protein diluent such as bovine serum albumin to prevent adsorptive losses to glassware at these low concentrations. For the treatment of DiGeorge Syndrome, the polypeptides may be administered at a rate of about 1.0 to 10 mg/kg of body weight. Generally, the same range of dosage amounts may be used in treatment of the other conditions or diseases mentioned.

The polypeptides are produced by the well known solid phase method as described by Stewart et al., *Solid Phase Peptide Synthesis*, Freeman and Co., San Francisco, 1969. As applied to some of the compounds of this invention, α-amino and hydroxyl protected tyrosine is attached to a benzhydrylamine polystyrene resin followed by removal of the α-amino protecting group with trifluoroacetic acid in methylene chloride, trifluoroacetic acid alone or HCl in dioxane. The deprotection is conducted at a temperature between about 0° C. and room temperature. Other standard cleaving reagents and conditions for removal of specific α-amino protecting groups may be used as described in Schroder E. Lubke, "The Peptides", 1, 72-75 (Academic Press, 1965). After removal of the α-amino protecting group the subsequent protected amino acids are coupled individually to the resin supported sequence, seriatim. Alternatively, small peptide fragments may be prepared by the solution method and introduced into the solid phase reactor in about a four fold excess. The coupling is carried out in dimethylformamide, methylene chloride, or a mixture of the two solvents. The success of each coupling reaction at each state of the synthesis is determined by the ninhydrin reaction as described by E. Kaiser et al., Analyt. Biochem., 34, 595 (1970). Where incomplete coupling has occurred, the reaction is repeated before the α-amino protecting group is removed for introduction of the next amino acid or amino acid sequence. The coupling reagent employed was diisopropylcarbodiimide.

After the desired amino acid sequence has been synthesized, the polypeptide is removed from the resin support by treatment with hydrogen fluoride and anisole to obtain the fully deprotected polypeptide. The polypeptide is then purified by gel filtration, high pressure preparative liquid chromatography and partition chromatography.

The ultimate fully protected, resin bound polypeptide of this invention specifically exemplified infra are $N^{\alpha}$-tert-butyloxycarbonyl-$N^g$-tosyl-L-arginyl-$N^\epsilon$-2-chlorobenzyloxycarbonyl-L-lysyl-L-asparaginyl-L-valyl-0-2,6-dichlorobenzyl-L-tyrosyl-benzhydrylamine polystyrene amide, and $N^{\alpha}$-tert-butyloxycarbonyl-$N^g$-tosyl-D-arginyl-$N^\epsilon$-2-chlorobenzyloxycarbonyl-L-lysyl-L-asparaginyl-L-valyl-D-phenylalanyl-benzhydrylamine polystyrene amide resin.

The protecting groups employed throughout the solid phase synthesis are well known to the art. The α-amino protecting groups employed with each amino acid introduced in sequence of the ultimate polypeptide are of the (1) acyl type protecting groups illustrated by the following: formyl, trifluoroacetyl, phthalyl, p-toluenesulfonyl (tosyl), nitrophenylsulfenyl, etc.; (2) aromatic urethane type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethane protecting groups illustrated by tert-butyloxycarbonyl, diisopropylmethoxycarbonyl, isopropyloxycarbonyl, allyloxycarbonyl, 2,2,2-trichloroethoxycarbonyl, amyloxycarbonyl; (4) cycloalkyl urethane type protecting groups illustrated by cyclopentyloxycarbonyl, adamantyloxycarbonyl, cyclohexyloxycarbonyl; (5) thio urethane type protecting groups such as phenylthiocarbonyl; (6) alkyl type protecting groups as illustrated by triphenylmethyl (trityl); (7) trialkylsilane groups such as trimethylsilane. The preferred α-amino protecting group is tert-butyloxycarbonyl.

Protection for the phenolic hydroxyl group, in amino acids such as D-tyrosine, may be by benzyl, 2,6-dichlorophenyl, benzyloxycarbonyl, 2-bromobenzyloxycarbonyl and the like.

Protection for the side chain amino group of amino acids such as lysine, may be by tosyl, t-amyloxycarbonyl, t-butyloxycarbonyl, diisopropyloxycarbonyl, benzyloxycarbonyl, halobenzyloxycarbonyl, nitrobenzyloxycarbonyl, and the like, the 2-chlorobenzyloxycarbonyl group being preferred.

In selecting a particular side-chain protecting group to be used in the synthesis of the peptides of this invention, the following rules should be followed: (a) the side-chain protecting group must be stable to the reagent and under the reaction conditions selected for removing the α-amino protecting group at each step of the synthesis, (b) the protecting group must retain its protecting properties (i.e. not be split off under coupling conditions), and (c) the side-chain protecting group must be removable upon the completion of the synthesis containing the desired amino acid sequence under reaction conditions that will not alter the peptide chain. The substituted pentapeptide wherein the terminal amino acid groups may be further substituted can be prepared by reaction of this basic pentapeptide with suitable reagents to prepared the desired derivatives. Reactions of this type such as acylation, esterification, amidation and the like, are of course well known in the art.

The following examples illustrate the preparation of L-arginyl-L-lysyl-L-asparaginyl-L-valyl-L-tyrosylamide triacetate and D-arginyl-L-lysyl-L-asparaginyl-L-valyl-D-phenylalanyl amide triacetate which are representative, in their solid phase preparation and biological activity, of the other compounds within the scope of the invention.

EXAMPLE 1

$N^\alpha$-tert-Butyloxycarbonyl-$N^g$-tosyl-L-arginyl-$N^\epsilon$-2-chlorobenzyloxycarbonyl-L-lysyl-L-asparaginyl-L-valyl-o-2,6-dichlorobenzyl-L-tyrosyl benzhydrylamine polystyrene amide Benzhydrylamine polystyrene resin (Bachem Inc.) 8 g. is treated according to Schedule A for amino group deprotection and amino acid coupling. The following protected amino acids are incorporated onto the resin to afford the title peptidoresin: Boc-Tyr(Cl$_2$Bzl)OH, Boc-Val-OH, Boc-Asn-OH (in the presence of N-hydroxybenzotriazole), Boc-Lys(ClZ)-OH and Boc-Arg(Tos)-OH.

Amino acid analysis: Asp (1) 1.14, Val (1) 1.13, Tyr (1) 0.90, Lys (1) 1, NH$_3$ (2) 4.86, Arg (1) 1.01.

Schedule A

1. Wash with CH$_2$Cl$_2$×3.
2. Treat with TFA-CH$_2$Cl$_2$-EDT (1:1:5%, v/v) for 3 minutes.
3. Treat as in 2 for 25 minutes.
4. Wash with CH$_2$Cl$_2$×3.
5. Wash with DMF.
6. Treat with 12% TEA in DMF twice for 3 minutes.
7. Wash with DMF.
8. Wash with CH$_2$Cl$_2$×3.
9. Treat with 4 equivalents of the corresponding amino acid derivative in CH$_2$Cl$_2$-DMF and stir for 5 minutes.
10. Add in two portions 5 equivalents of DIC dissolved in CH$_2$Cl$_2$ and over a period of 30 minutes. Reaction time 6 hours.
11. Wash with DMF×3.
12. Wash with CH$_2$Cl$_2$×3.
13. Test by ninhydrin reaction according to the procedure of Kaiser et al., *Annal. Biochem.*, 34, 595 (1970). In case of incomplete reaction, repeat steps 9 to 13, as above.

EXAMPLE 2

L-Arginyl-L-lysyl-L-asparaginyl-L-valyl-L-tyrosyl-amide triacetate salt

The peptidoresin of the previous example (11 g.) is mixed with anisole (22 ml.) and treated with 150 ml. liquid HF in the absence of air and in an ice bath for 1 hour. The excess HF is removed in vacuo as fast as possible and the residue is taken in 80% aqueous AcOH, filtered and evaporated to dryness in a rotary evaporator. The residue is chromatographed through a column (2.5×90 cm.) of Sephadex G-10 and eluted with 50% aqueous AcOH. The material which emerges in fractions (8 ml. each) 30-40 is pooled and lyophilized to yield 1.2 g. of product. This material is subjected to preparative high pressure liquid chromatography through one column of Prep-PAK-500/C-18 cartridge (5.7×30 cm.) Waters Associates and eluted with a solvent mixture of 95% 0.1 M NH$_4$OAc, pH 4 and 5% CH$_3$CN. The material which emerges between 1200 and 2100 ml. is pooled and lyophilized to give 859 mg. of a solid which on TLC (Avicel plates) (EtOAc-n-BuOH-H$_2$O-AcOH, 1:1:1:1, v/v) shows a main spot at R$_f$0.63 and a minor at R$_f$0.46. This material is subjected to partition chromatography through a column of Sephadex G-25 (2.5×89 cm.) with the biphasic system n-BuOH-H$_2$O-AcOH, 4:5:1, v/v. The column is eluted first with 2 liters of the upper phase of the above system and then with 20% aqueous AcOH. The material which emerges is pooled and lyophilized to yield 343 mg. of the title compound.

TLC, Avicel precoated glass plates, Analtech.
$R_f$(EtOAc-n-BuOH-H$_2$O-AcOH, 1:1:1:1, v/v) 0.59.
$R_f$ (EtOAc-n-BuOH-H$_2$O-AcOH-Pyridine, 1:1:1:0.5:0.5, v/v) 0.49.

Amino acid analysis: Asp (1) 1.02, Val (1) 0.90, Tyr (1) 0.90, Lys (1) 1, Arg (1) 0.99, NH$_3$ (2) 2.01.

EXAMPLE 3 tert-Butyloxycarbonyl-N$^g$-tosyl-D-arginyl-$\epsilon$-2-chlorobenzyloxycarbonyl-L-lysyl-L-asparaginyl-L-valyl-D-phenylalanylbenzhydrylamine polystyrene amide resin Benzhydrylamine polystyrene resin (Bachem Inc.) 9 g. with an —NH$_2$ content of approximately 0.4 mmoles/g. is placed in a reaction vessel of a peptide automatic synthesizer Beckman 990A and subjected to cycles according to Schedules 1 and 2, for the incorporation of Boc-D-Phe-OH and Boc-Val-OH. Schedule 1 is used exclusively for the incorporation of Boc-Asn-OH in the presence of 1 equivalent of N-hydroxybenzotriazole and Boc-Lys-(ClCBz)-OH and Boc-D-Arg(Tos)-OH. The deprotection of the α-amino group is carried out by treatment with a mixture of TFA-CH$_2$Cl$_2$-EDT (1:1:4%, v/v) for a total of 30 minutes. Neutralization of the TFA salt is carried out by 12% NEt$_3$ in DMF and coupling of the next protected amino acid is achieved by DCC 1 M solution in DMF for 3 hours.

Schedule 1

1. Wash with CH$_2$Cl$_2$ × 3.
2. Treat with TFA-CH-2Cl$_2$-EDT, 1:1:5% for 5 minutes.
3. Repeat (2) for 25 minutes.
4. Wash with CH$_2$Cl$_2$ × 4.
5. Treat with TEA 12% in DMF for 1 minute.
6. Repeat (5) for 5 minutes.
7. Wash with CH$_2$Cl$_2$ × 3.
8. Add 4 equivalents of Boc-protected amino acid and stir for 5 minutes.
9. Add 2 equivalents of 1 M-DIC solution in DMF and stir for 25 minutes.
10. Add 2 equivalents of 1 M-DIC solution in DMF and stir for 180 minutes.
11. Wash with CH$_2$Cl$_2$ × 3.
12. Wash with methanol × 3.
13. Wash with CH$_2$Cl$_2$ × 3.

Schedule 2

1. Wash with CH$_2$Cl$_2$ × 3.
2. Add 3 equivalents of Boc-protected amino acid and stir for for 5 minutes.
3. Add 2 equivalents of 1 M-DIC solution in DMF and stir for 180 minutes.
4. Wash with DMF × 3.
5. Wash with CH$_2$Cl$_2$ × 3.
6. Wash with methanol × 3.
7. Wash with CH$_2$Cl$_2$ × 3.

EXAMPLE 4

D-Arginyl-L-lysyl-L-asparaginyl-L-valyl-D-phenylalanyl amide tri acetate salt

The peptidoresin of Example 3 (11 g.) is mixed with anisole 22 ml. and treated with 150 ml. of liquid HF in the absence of air and in an ice bath for 1 hour. The excess HF is removed in vacuo as fast as possible (ca. 2 hours) and the residue is extracted with 80% aqueous AcOH, filtered, and the filtrate after dilution is lyophilized to yield 2.16 g. This material is applied onto a column of Sephadex G-10 (2.5 × 90 cm.) and is eluted with 50% aqueous AcOH. The material which emerges in fractions (4.5 ml. each) 27 to 44 is pooled and lyophilized to give 1.3 g. of solid material.

Amino acid analysis: Asp (1) 1.04, Val (1) 0.62, Phe (1) 0.66, Lys (1) 1.00, NH$_3$ (2) 1.95, Arg (1) 1.00.

The above material is purified further by preparative HPLC through one column of Prep-PAK-500/C$_{18}$ Cartridge, (5.7 × 30 cm.) Waters Associates, and eluted with a solvent mixture of 85% 0.1 N-NH$_4$OAc and 15% CH$_3$CN adjusted to pH 4 (Flow rate, 250 ml/min.). The material which emerges between 5,250 and 6,750 ml. is pooled and lyophilized until free of NH$_4$OAc to give 504 mg. of the title compound.

TLC Avicel precoated glass plates.
$R_f$(EtOAc-n-BuOHOH$_2$O-AcOH, 1:1:1:1, v/v) 0.71.
Silica gel 60 F-254 precoated glass plates. $R_f$ (solvent system as above) 0.20.

Amino acid analysis: Asp (1) 1, Val (1) 0.92, Phe (1) 0.90, Lys (1) 1, NH$_3$ (2) 1.92, Arg (1) 1.01.

The activity of the compounds of Example 2 and Example 4 was determined according to the following procedure:

T lymphocytes are isolated from spleens of male CBA/J or NZB mice. Cell homogenates are prepared in Hank's balanced salt solution (HBSS). After removal of larger particles and repeated washing of the cells in HBSS they are suspended in minimum essential medium (MEM) and passed through a glass wool column to remove macrophages. The cells are then incubated on a nylon wool column at 37° C., 95% air, 5% CO$_2$, for 45 minutes. The non-adherant T lymphocytes are then eluted from the column, counted, and adjusted to 20 × 10$^6$ cells/ml. 50 μl of cells are cultured (37° C., 95% air, 5% CO$_2$) with compound, for 48 hours before the addition of 0.5 μCi. of 3H-thymidine for the last 16 hours of culture. The total volume of the culture system is 200 μl. The cells are then harvested on a multiple automatic sample harvester (Mash II), the glass fiber filter disks placed in 10 ml. of xylene base scintillation fluid, and counted for 1 minute in a liquid scintillation counter. Results are reported as CPM ± SE. Comparisons are made between counts obtained with control cultures and cultures containing compound and a determination made as to whether the compounds are active at the dosage tested. The findings are summarized in Table 1.

TABLE I

| Compound | Concentration (μg/culture) | Activity |
|---|---|---|
| Arg—Lys—Asn—Val—Tyr—NH$_2$ | 0.2 | IA |
|  | 0.1 | A |
|  | 0.05 | A |
|  | 0.025 | A |
|  | 0.006 | A |
|  | 0.0015 | A |
| D-Arg—Lys—Asn—Val—D-Phe—NH$_2$ | 0.1 | A |
|  | 0.025 | A |
|  | 0.006 | A |
|  | 0.0015 | A |

A = Active
IA = Inactive

The results show that the peptides have marked activity in stimulating the proliferation of T-cells at very low concentration levels.

What is claimed is:

1. A polypeptide having the following formula:

R-X$_1$-Lys-X$_3$-Val-X$_5$-R$_1$ wherein
R is hydrogen, alkanoyl of 1-4 carbon atoms or aroyl of 6-10 carbon atoms;
X$_1$ is L-Arg, D-Arg or D-homoarginine;
X$_3$ is Asn, Gln or the N-substituted carboxamides thereof;
X$_5$ is L- or D-Tyr, L- or D-Phe, L- or D-Trp, L- or D-Leu, L- or D-Met, D-Met-ol-oxide or D-Phe-ol; and
R$_1$ is amino, monoalkylamino of 1-4 carbon atoms, dialkylamino of 1-4 carbon atoms, hydroxy, alkoxy of 1-4 carbon atoms,

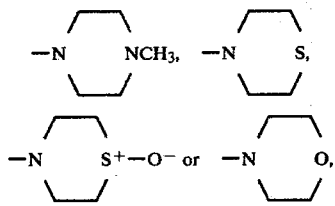

or the fully protected peptide-resin intermediates thereof, or pharmaceutically acceptable salts thereof.

2. A polypeptide having the following formula:

R-X$_1$-Lys-X$_3$-Val-X$_5$-R$_1$ wherein
R is hydrogen, alkanoyl of 1-4 carbon atoms or aroyl of 6-10 carbon atoms;
X$_1$ is L-Arg, D-Arg or D-homoarginine;
X$_3$ is Asn, Gln or the N-substituted carboxamides thereof;
X$_5$ is L- or D-Phe, L- or D-Trp, L- or D-Leu, L- or D-Met, D-Met-ol-oxide or D-Phe-ol; and
R$_1$ is amino, monoalkylamino of 1-4 carbon atoms, dialkylamino of 1-4 carbon atoms, hydroxy, alkoxy of 1-4 carbon atoms,

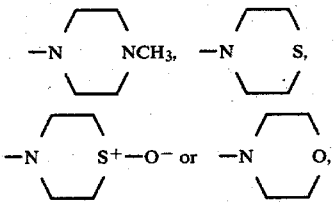

or the fully protected peptide-resin intermediates thereof, or pharmaceutically acceptable salts thereof.

3. The compound of claim 1, which is Arg-Lys-Asn-Val-Tyr-NH$_2$ or a pharmaceutically acceptable salt thereof.

4. The compound of claim 1, which is D-Arg-Lys-Asn-Val-D-Phe-NH$_2$ or a pharmaceutically salt thereof.